US012139087B1

(12) United States Patent
Zeng et al.

(10) Patent No.: US 12,139,087 B1
(45) Date of Patent: Nov. 12, 2024

(54) METHODS AND SYSTEMS FOR ESTIMATING VITAL SIGNS OF VEHICLE OCCUPANTS USING ULTRA WIDEBAND

(71) Applicant: Robert Bosch GmbH, Stuttgart (DE)

(72) Inventors: Yunze Zeng, San Jose, CA (US); Vivek Jain, Sunnyvale, CA (US)

(73) Assignee: Robert Bosch GmbH (DE)

( * ) Notice: Subject to any disclaimer, the term of this patent is extended or adjusted under 35 U.S.C. 154(b) by 0 days.

(21) Appl. No.: 18/236,492

(22) Filed: Aug. 22, 2023

(51) Int. Cl.
*B60R 21/015* (2006.01)
*G01S 13/02* (2006.01)
(52) U.S. Cl.
CPC .... *B60R 21/01534* (2014.10); *G01S 13/0209* (2013.01)
(58) Field of Classification Search
CPC ............. B60R 21/01534; G01S 13/0209
See application file for complete search history.

(56) References Cited

U.S. PATENT DOCUMENTS

| 2020/0309932 A1* | 10/2020 | Zeng ................. G07C 5/08 |
| 2020/0348406 A1* | 11/2020 | Jain .................. G01S 13/0209 |
| 2022/0128678 A1* | 4/2022 | Abdul Kareem ....... G01S 7/038 |
| 2022/0373646 A1* | 11/2022 | Nguyen ............... A61B 5/0255 |
| 2023/0074421 A1* | 3/2023 | Kim ................... G01S 7/006 |
| 2023/0319811 A1* | 10/2023 | Jain ...................... H04B 1/69 |
| 2023/0345603 A1* | 10/2023 | Tertinek ............. H05B 47/115 |
| 2024/0053466 A1* | 2/2024 | Naka ................... G01S 13/06 |
| 2024/0054885 A1* | 2/2024 | Ette ................... G01S 13/0209 |

FOREIGN PATENT DOCUMENTS

| CN | 114407777 A | * | 4/2022 | |
| EP | 3739356 A1 | * | 11/2020 | ........... G01P 15/18 |
| EP | 4112370 A1 | * | 1/2023 | ........... B60L 3/0015 |
| KR | 20230036023 A | * | 3/2023 | |
| WO | WO-2021220190 A1 | * | 11/2021 | ........... A61B 5/0205 |
| WO | WO-2024028198 A1 | * | 2/2024 | ........... G01S 7/006 |

* cited by examiner

*Primary Examiner* — Drew J Brown
(74) *Attorney, Agent, or Firm* — Dickinson Wright PLLC

(57) ABSTRACT

Methods and systems for estimating vital signs of vehicle occupants using Ultra-Wideband communication. UWB signals are transmitted from one UWB system node to another UWB system node. Channel impulse responses (CIRs) associated with the UWB signals are determined. Based on the CIRs, in some embodiments velocities associated with the UWB signals are determined, and activities of vehicle occupants are classified based on the CIRs along with vital signs such as breathing rates. In other embodiments, based on the CIRs, phase unwrapping of phase features associated with the CIRs is performed, and principle component analysis (PCA) transforms the CIRs, allowing estimated vital signs such as breathing rates to be determined.

20 Claims, 12 Drawing Sheets

METHODS AND SYSTEMS FOR ESTIMATING VITAL SIGNS OF VEHICLE OCCUPANTS USING ULTRA WIDEBAND

TECHNICAL FIELD

The present disclosure relates to methods and systems for estimating vital signs of vehicle occupants using Ultra-Wideband (UWB) communication.

BACKGROUND

For automotive applications, keyless entry systems provide remote access allowing users the ability to remotely lock or unlock vehicle doors. For instance, key fobs include buttons for locking/unlocking vehicle doors. More recently, automotive manufacturers have introduced passive keyless system. Passive keyless systems may not require pressing a button to lock/unlock vehicle doors. Passive keyless systems also may not require a physical key to start the vehicle. Instead, passive keyless systems may allow such actions to be performed when the key fob is located near or within the vehicle. Such systems can rely on radio frequency (RF) signals, but can be limited beyond these applications.

SUMMARY

According to an embodiment, a method of estimating vital signs of vehicle occupants using Ultra-Wideband communication includes: transmitting Ultra-Wideband (UWB) signals from a first UWB system node within a vehicle; receiving the UWB signals at a second UWB system node within the vehicle; computing channel impulse responses (CIRs) associated with the UWB signals received at the second UWB system node; based on the CIRs, calculating velocities associated with the UWB signals; classifying an activity of a vehicle occupant as breathing based on the calculated velocities falling between a lower threshold and an upper threshold; and estimating a breathing rate of the vehicle occupant based on the calculated velocities.

According to another embodiment, a method of estimating vital signs of vehicle occupants using UWB communication includes: transmitting UWB signals from a first UWB system node within a vehicle; receiving the UWB signals at a second UWB system node within the vehicle; computing channel impulse responses (CIRs) associated with the UWB signals received at the second UWB system node; performing a phase unwrapping of phase features associated with the CIRs; truncating the CIRs to select a chunk of CIR taps; performing a principle component analysis (PCA) transformation on the CIR taps to project CIR data onto a hyperplane; applying a band-pass filter to the projected CIR data to remove high-frequency components associated with the projected CIR data, wherein the applying yields filtered projected CIR data; and estimating the breathing rate of the vehicle occupant based on the filtered projected CIR data.

According to another embodiment, a system is configured to estimate vital signs of vehicle occupants using UWB communication. The system includes a transmitting node operable to transmit UWB signals; a receiving node operable to receive the UWB signals, wherein the UWB signals include channel impulse responses (CIRs); and a processor in communication with transmitting node and the receiving node, wherein the processor is programmed to receive the UWB signals at the receiving node; extract the CIRs from the UWB signals received at the receiving node; based on the CIRs, calculate velocities associated with the UWB signals; and estimate a breathing rate of a vehicle occupant based on the calculated velocities

DETAILED DESCRIPTION

Figure 1A:
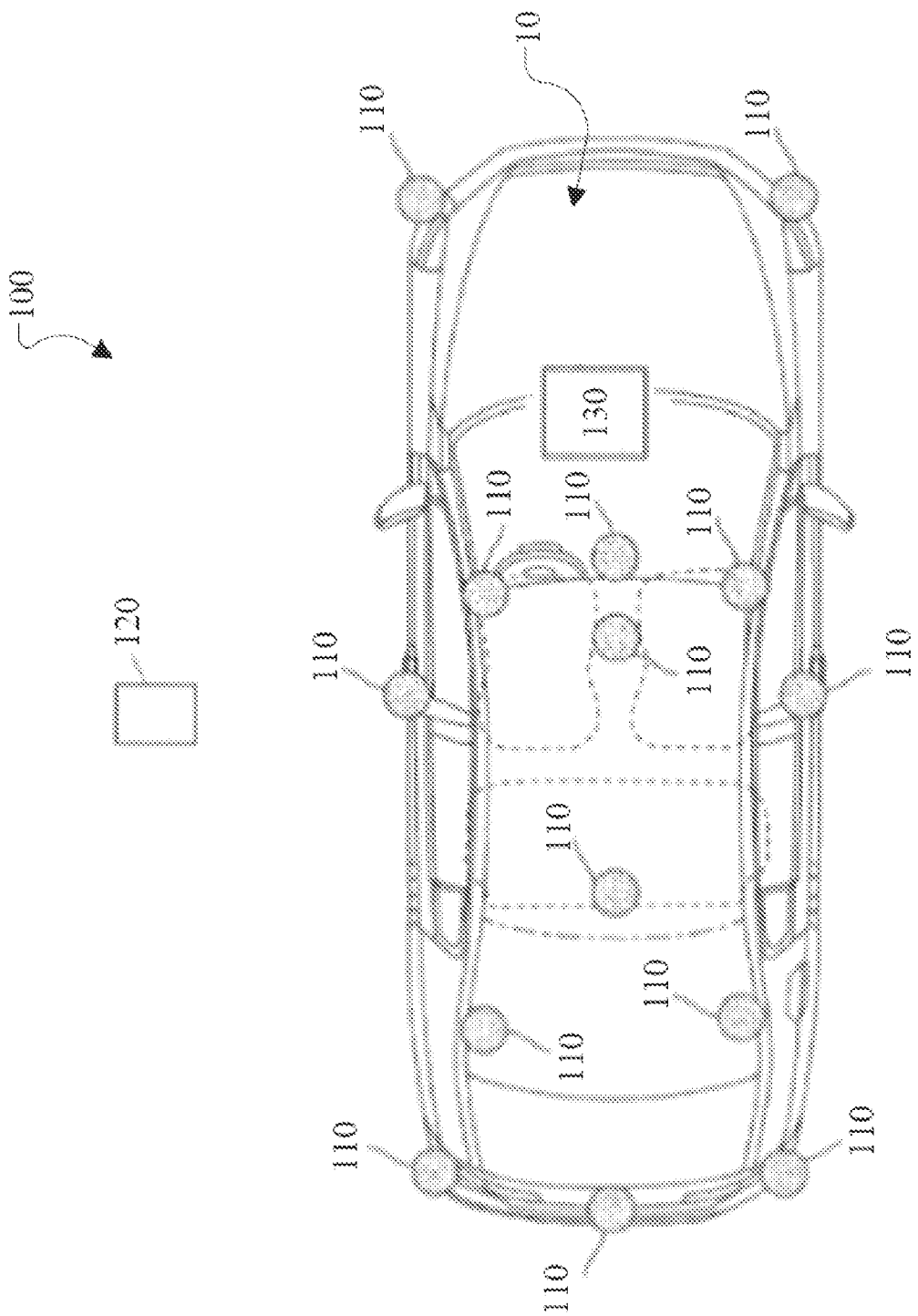
FIG. 1A is an illustrative example of a vehicle system having an ultra-wide band (UWB) infrastructure and sensing system located within a vehicle.

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

The words "a", "an", and "the" as used herein refers to both singular and plural referents unless the context clearly dictates otherwise. By way of example, "a processor" programmed to perform various functions refers to one processor programmed to perform each and every function, or multiple processors collectively programmed to perform the various functions. By way of another example, "a system node" configured to transmit a UWB signal and receive a UWB signal refers to (1) one system node transmitting the UWB signal and that same node receiving a UWB signal, or (2) one system node transmitting a UWB signal and a different system node receiving the UWB signal.

With the ongoing advancements in wireless technologies, people now use any number of connected and personalized services. As the number of wireless systems and services increases, manufacturers have begun to leverage such pre-existing systems and services in a different way than what was originally contemplated. For instance, manufacturers have begun to leverage radio frequency (RF) transceivers (such as WiFi) to track movement of humans through walls and behind closed doors. The use of WiFi to track movement is much different than its original use-case of communicating data between electronic devices. By leveraging a pre-existing system beyond its original intended application, manufacturers have been able to reduce the need for extra hardware which in turn reduces cost, saves space, and/or provides increased power savings.

In automotive applications, key fobs have become common to perform various functions. For instance, when a user is located within the vicinity of a vehicle, the key fob may be used to automatically unlock doors. Or, when a user is located within the vehicle, the key fob may allow the user to start the vehicle by merely the push of a button. To perform these functions, a key fob wirelessly communicates with the vehicle to perform an authentication process. Currently, automotive manufacturers may rely on two types of radio frequency (RF) technologies. For passive entry systems (PES) and comfort entry go (CEG) applications, a low frequency (LF) technology may be used for key fob proximity and localization. For remote keyless entry, ultra-high frequency (UHF) technology may be employed. However, traditional LF and UHF technologies may not be adequate for additional leveraging beyond this original intended use. For instance, traditional LF and UHF technologies may not be capable of performing detection of users within a vehicle. As a result, additional systems may be required to perform such functionality. Also, LF and UHF systems have been known to be subjected to security breaches including "relay" attacks.

As disclosed by U.S. Pat. No. 10,573,104, which is incorporated herein by reference, an Ultra-Wideband (UWB) system is disclosed and operable to perform certain automotive functions such as vehicular access (i.e., keyless entry). UWB technology may be preferred over LF and UHF technology because it may provide more robust functionality and improved security capabilities. It is contemplated that a UWB system may also be capable of providing increased context awareness, safety, and security applications.

FIG. 1A is a diagram of an example of a vehicle system 100 with an UWB infrastructure that provides a vehicle access system and also in-vehicle sensing according to an example embodiment. In this embodiment, the system 100 includes a plurality of system nodes 110 arranged at various locations of a vehicle 10. It is appreciated that the particular number of system nodes 110 and particular locations of the system nodes 110 depends on the desired accuracy and performance, as well as the particular make and model of the vehicle 10. The system nodes 110 are configured to communicate with a target device 120 (which may be mobile and/or portable) to determine a relative position and/or location of the target device 120. In an example embodiment, the system 100 may be configured such that a particular system node is designated as a master system node and other system nodes are designated as slave system nodes such that master system node controls communications with the slave system nodes and collects data from the slave system nodes S for the purpose of localizing the target device 120. Processing of the data collected from the system nodes 110 to localize the target device 120 is performed by the master system node or a processing system 130. In an example embodiment, the processing system 130 is or includes an electronic control unit (ECU). In at least one embodiment, UWB communications are utilized between the system nodes 110 and the target device 120 to enable localization thereof. Each system node 110 is a communication system node 110A or a dual-mode system node 110B. Either system node 110A or 110B can be referred to as a UWB system node, even though the system node may be configured for other types of additional communication.

Figure 1B:
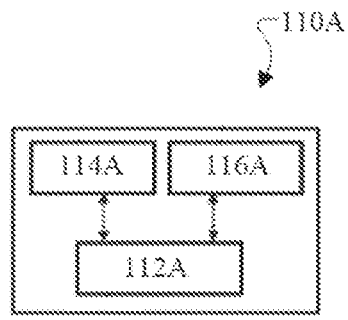
FIG. 1B is a diagram of an example of a communication system node according to an example embodiment of this disclosure.

FIG. 1B shows an example of a communication system node 110A according to an embodiment. In the illustrated embodiment, each communication system node 110A comprises a processor 112A, memory 114A, and a transceiver 116A. The memory 114A is configured to store program instructions that, when executed by the processor 112A, enable the respective communication system node 110A to perform various operations described elsewhere herein, including localization of the target device 120 and sensing of a predetermined region. The memory 114A may be of any type of device capable of storing information accessible by the processor 112A, such as write-capable memories, read-only memories, or other non-transitory computer-readable mediums. Additionally, the processor 112A includes any hardware system, hardware mechanism or hardware component that processes data, signals, or other information. The processor 112A may include a system with a central processing unit, multiple processing units, dedicated circuitry for achieving functionality, or other systems. In an example, the communication system node 110A includes a microcontroller, which contains at least the processor 112A and the memory 114A along with programmable input/output peripherals.

The transceiver 116A includes at least a UWB transceiver configured to communicate with the target device 120 and may include any of various other devices configured for communication with other electronic devices, including the ability to send communication signals and receive communication signals. In some embodiments, the transceiver 116A comprises multiple UWB transceivers and/or multiple UWB antennas arranged in an array. In an example embodiment, the transceiver 116A includes at least one further transceiver configured to communicate with the other system nodes 110 (e.g., communication system nodes 110A, dual-mode nodes 110B, etc.), the target device 120, and/or the processing system 130, via a wired or wireless connection.

Figure 1C:
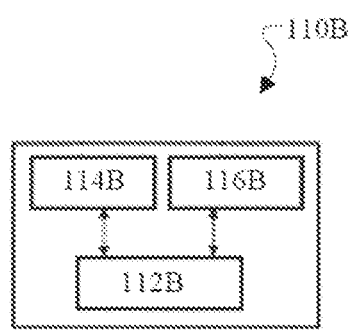
FIG. 1C is a diagram of an example of a dual-mode system node according to an example embodiment of this disclosure.

FIG. 1C shows an example of a dual-mode system node 110B according to an embodiment. The dual-mode system node 110B is configured to switch between a UWB communication mode and a UWB radar mode. More specifically, in the illustrated embodiment, the dual-mode system node 110B comprises at least a processor 112B, a memory 114B, and a transceiver 116B. The processor 112B includes any hardware system, hardware mechanism or hardware component that processes data, signals, or other information. The processor 112B may include a system with a central processing unit, multiple processing units, dedicated circuitry for achieving functionality, a digital signal processor (DSP), or other processing technology. The memory 114B is configured to store program instructions that, when executed by the processor 112B, enable the respective system node 110 to perform various operations described elsewhere herein, including localization of the target device 120, sensing of a sensing region, switching between communication mode and radar mode, performing signal processing, etc. The memory 114B may be of any type of device capable of storing information accessible by the processor 112B, such as write-capable memories, read-only memories, or other non-transitory computer-readable mediums. In an example, the dual-mode system node 110B includes a microcontroller, which contains at least the processor 112B and the memory 114B along with programmable input/output peripherals.

The transceiver 116B includes at least a transceiver, which is configured switch between transmitting/receiving UWB communication and transmitting/receiving UWB radar, respectively. The transceiver 116B is configured to communicate with the target device 120 and may include any of various other devices configured for communication with other electronic devices, including the ability to send communication signals and receive communication signals. In some embodiments, the transceiver 116B comprises multiple UWB transceivers and/or multiple UWB antennas arranged in an array. The multiple UWB transceivers and/or multiple UWB antennas are configured to transmit/receive UWB communications and UWB radar, respectively. In an example embodiment, the transceiver 116B includes at least one further transceiver configured to communicate with the other system nodes 110 (e.g., communication system nodes 110A, dual-mode system nodes 110B, etc.), the target device 120, and/or the processing system 130, via a wired or wireless connection.

The dual-mode system node 110B is operable to switch between communication mode and radar mode, respectively. Also, the dual-mode system node 110B is operable to transmit pulses in radar mode and communication mode, respectively. The duration of those pulses and/or number of those transmitted pulses differs in these two distinct modes. For example, one or more pulses generated in the radar mode differ from one or more pulses generated in communication mode with respect to pulse shape, repetition frequency, pulse power, number of pulses, duration of pulse transmission, any appropriate pulse feature, or any number and combination thereof.

In an example embodiment, for instance, the dual-mode system node 110B includes one or more switching mechanisms, implemented via hardware, software, or a combination thereof, which is configured to provide the communication mode and the radar mode, respectively, and enable the dual-mode system node 110B to switch between these two modes. As a non-limiting example, for instance, the dual-mode system node 110B may include a switch connected to an antenna and a radio integrated circuit (IC), which may be present in FIG. 1C but not shown in this high-level block diagram. This switch controls whether an antenna is connected to at least one transmitting or receiving circuit. Further, this switch controls whether the antenna is connected to radar receiving circuit or communication mode receiving circuit. In the case that there are multiple antennas in the dual-mode system node 110B, then the dual-mode system node 110B may include a switch per antenna to control its operation (e.g., transmitting or receiving) or a switch to choose an antenna and a switch to enable operation (e.g., transmitting or receiving radar or receiving communication).

As discussed above, the dual-mode system node 110B is advantageously configured to selectively switch between radar mode and communication mode. More specifically, the dual-mode system node 110B is configured to operate in communication mode or radar mode. For example, when in communication mode, each dual-mode system node 110B is enabled to contribute to in-vehicle sensing throughout the vehicle 10 via UWB communication. And, when in radar mode, each dual-mode system node 110B is operable to provide targeted sensing for specific locations (e.g. seats). In addition, the use of UWB radar contributes to providing health status data (e.g., heart rates, breathing rates) of at least one living being in the vehicle 10, as will be described further herein.

Figure 1D:
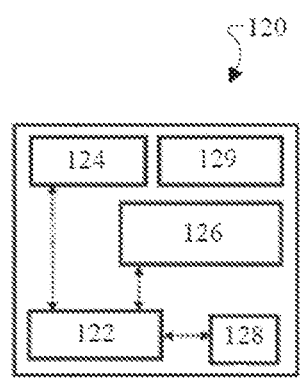
FIG. 1D is a diagram of an example of a target device according to an example embodiment of this disclosure.

FIG. 1D shows a non-limiting example of the target device 120, which may comprise a key-fob, a smart phone, a smart watch, or any suitable electronic device. In the illustrated embodiment, the target device 120 comprises at least a processor 122, memory 124, transceivers 126, an I/O interface 128, and a battery 129. The memory 124 is configured to store program instructions that, when executed by the processor 122, enable the target device 120 to perform various operations described elsewhere herein, including communicating with the system nodes 110 for the purpose of localizing the target device 120. The memory 124 may be of any type of device capable of storing information accessible by the processor 122, such as a memory card, ROM, RAM, hard drives, discs, flash memory, or other non-transitory computer-readable mediums. Additionally, the processor 122 includes any hardware system, hardware mechanism or hardware component that processes data, signals or other information. The processor 122 may include a system with a central processing unit, multiple processing units, dedicated circuitry for achieving functionality, or other systems.

The transceivers 126 includes at least an UWB transceiver configured to communicate with the system nodes 110 (e.g., communication system nodes 110A, dual-mode nodes 110B, etc.) and may also include any of various other devices configured for communication with other electronic devices, including the ability to send communication signals and receive communication signals. In an example embodiment, the transceivers 126 further include additional transceivers which are common to smart phones and/or smart watches, such as Wi-Fi or Bluetooth® transceivers and transceivers configured to communicate via for wireless telephony networks. The I/O interface 128 includes software and hardware configured to facilitate communications with the one or more interfaces (not shown) of the target device 120, such as tactile buttons, switches, and/or toggles, touch screen displays, microphones, speakers, and connection ports. The battery 129 is configured to power the various electronic devices of the target device 120 and may comprise a replaceable or rechargeable battery.

In an example embodiment, the processing system 130 is configured to control and monitor various electronic functions relating to the vehicle 10. The processing system 130 may be in communication with the nodes 110 for operating the nodes and/or processing data received by the nodes. For example, the nodes 110 may be used to perform the automotive functions described herein, such as starting the vehicle 10 when the processing system 130 determines target device 120 is located within the vehicle 10. The system 130 may also be operable to perform the following functions: (1) detecting the state of the vehicle 10 (e.g., whether the vehicle 10 is unoccupied or occupied; or whether a door, window, or trunk is open); (2) monitoring the vital signs of an occupant within the vehicle 10 (e.g., heart rate, breathing rate, or user emotional state); (3) determining the occupancy of the vehicle 10 (i.e., count the number of living beings, humans and animals, within the vehicle 10); (4) detecting human movement or activity in or near the vehicle; (5) detecting the occupancy when a driver/passenger approaches (or leaves) the vehicle 10; and (6) detecting an intrusion in the vehicle 10 while ensuring complete privacy. Various warnings can be triggered based on these detections; for example, if the breathing rate of the occupant is present while the driver exits the vehicle, the vehicle can warn the driver that a passenger is still in the back seat of the vehicle, which reminds the driver to check for other passengers in the vehicle before leaving the vehicle unattended. In another embodiment, if the breathing rate of the occupant is above a threshold, it can indicate a certain mood or health of the occupant, and an appropriate message or warning can be delivered to the driver alerting the driver of the mood or health. The processing system 130 includes at least one electronic control unit (ECU). In an example, the processing system 130 includes a microcontroller and/or microprocessor. In an example, the processing system comprises at least a processor, a memory, and an I/O interface. The memory is configured to store program instructions that, when executed by the processor, enable the processing system 130 to perform various operations described elsewhere herein, including localization of the target device 120, sensing one or more sensing regions, and using UWB radar to providing health status data (e.g., heart rates, breathing rate, emotional state) of at least one living being in the vehicle 10. The memory may be of any type of device capable of storing information accessible by the processor, such as a memory card, ROM, RAM, hard drives, discs, flash memory, or other computer-readable medium. Additionally, the processor includes any hardware system, hardware mechanism or hardware component that processes data, signals or other information. The processor may include a system with a central processing unit, multiple processing units, dedicated circuitry for achieving functionality, or other systems. The I/O interface includes software and hardware configured to facilitate monitoring and control of various electronics and their functions.

Figure 2:
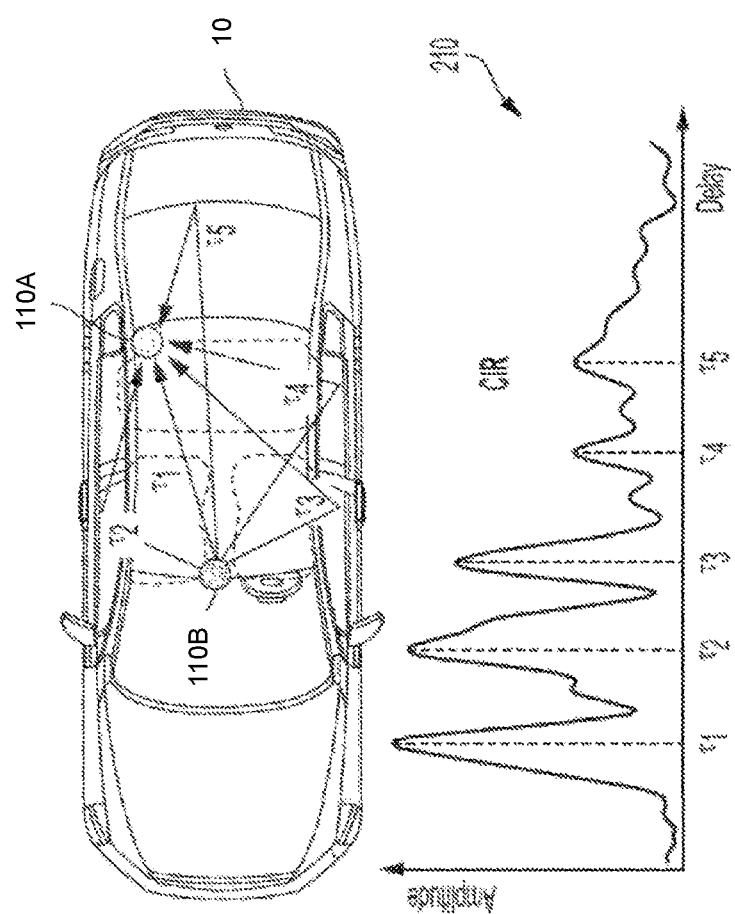
FIG. 2 is an illustrative example of the channel impulse response (CIR) signals seen by the UWB nodes in the vehicle system.

The various nodes 110 (including nodes 110A and/or 110B) may be operable as a transceiver for sending and receiving a UWB message. One or more of nodes 110 may periodically transmit (or blink) a UWB message. One or more nodes 110 may perform the UWB-based sensing of car states or occupancy vitals using the channel state information such as channel impulse response (CIR) computed by a given receiver. For instance, FIG. 2 illustrates node 110B transmitting a UWB message that may be received by node 110A. Of course, either node 110A or 110B may be a different type of node described herein, and this is merely one example shown. As illustrated, a UWB message may be reflected at various points (shown by $\tau_1$-$\tau_5$) around the vehicle 102.

The CIR of the UWB signals generally refers to the response of the wireless communication channel though which the signal travels. As they UWB signals are transmitted from one node and received by another node, during the transmission the signal encounters various obstacles and environmental factors that cause the signal to attenuate, scatter, and reflect. One of these obstacle can be a human occupant within the vehicle. The CIR describes how the channel behaves in the time domain. It represents the time-varying characteristics of the channel, including the delays, attenuations, and phase shifts that the signal experiences while traveling from the transmitter to the receiver.

Graph 210 illustrates the CIR that may be computed by node 110A based on the reflected UWB message. As shown, the CIR for TI may have the greatest amplitude and the least amount of time delay because it was not reflected at any point within vehicle 10 between being sent from node 110B to node 110A. Conversely, the CIR for $\tau_5$ may have one of the smallest amplitudes and the largest delays because it was reflected by a rear point (e.g., the trunk) of the vehicle 10 before being received by node 118. The other CIRs $\tau_2$, $\tau_3$, and $\tau_4$ may have different amplitudes and delays based upon their traveled path and their reflection within the vehicle 10.

Figure 3A:
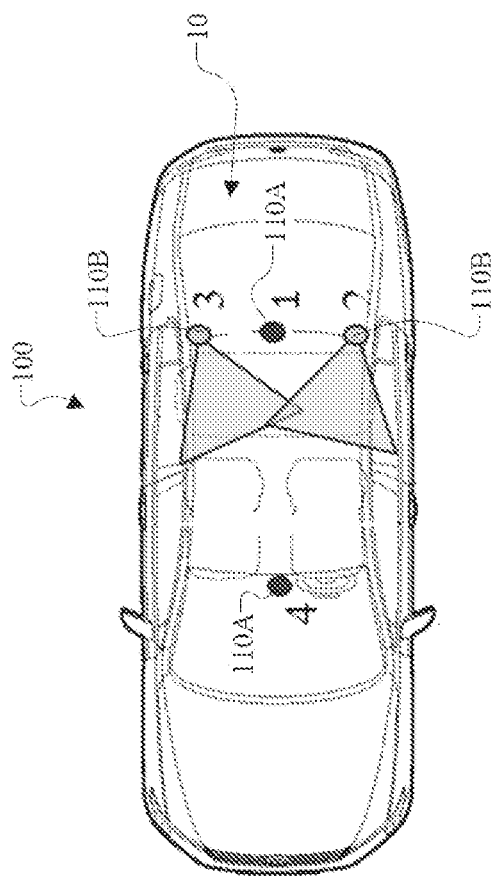
FIG. 3A is a diagram of an example of a set of system nodes that include dual-mode system nodes with respect to a vehicle according to an example embodiment of this disclosure.
Figure 3B:
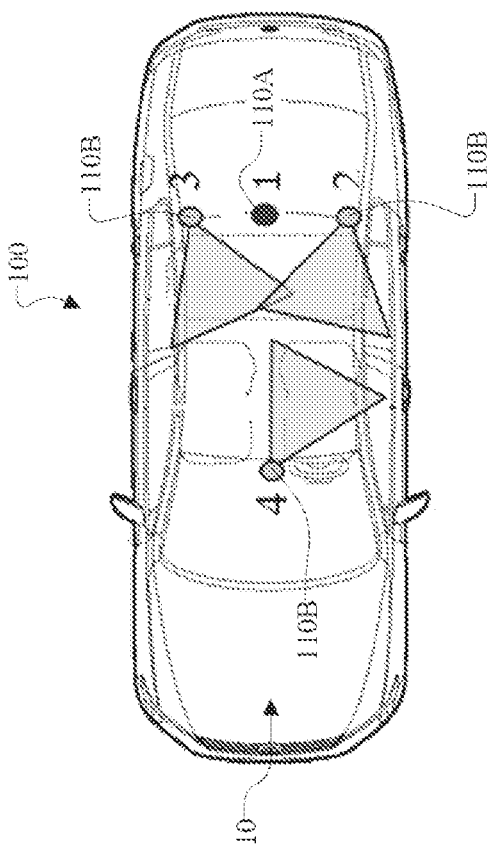
FIG. 3B is a diagram of an example of another set of system nodes that include dual-mode system nodes with respect to a vehicle according to an example embodiment of this disclosure.

FIG. 3A and FIG. 3B illustrate non-limiting examples of sets of system nodes with respect to the vehicle 10 according to an example embodiment. FIG. 3A and FIG. 3B illustrate examples with at least one communication system node 110A and at least one dual-mode system node 110B. In this regard, FIG. 3A and FIG. 3B illustrate non-limiting examples of node arrangements with respect to the vehicle 10. In addition, FIG. 3A and FIG. 3B include non-limiting conceptual representations of the sensing regions of the dual-mode system nodes 110B in the form of shaded triangles. The embodiments are not limited to these node arrangements, as there are a number of other node arrangements. FIG. 3A and FIG. 3B also illustrate examples of node arrangements in which UWB radar and UWB communications are combinable to provide sensing state data and/or sensing applications.

FIG. 3A illustrates a first arrangement that includes a UWB communication system node 110A at the first location (labeled as 1), a UWB dual-mode system node 110B at the second location (2), a UWB dual-mode system node 110B at the third location (3), and a UWB communication system node 110A at the fourth location (4). FIG. 3B illustrates a second arrangement that includes a UWB communication system node 110A at the first location (1), a UWB dual-mode system node 110B at the second location (2), a UWB dual-mode system node 110B at the third location (3), and a UWB dual-mode system node 110B at the fourth location (4). In this regard, the second node arrangement of FIG. 3B differs with respect to the first node arrangement of FIG. 3A in that the fourth location in FIG. 3B includes a dual-mode system node 110B whereas the fourth location in FIG. 3A includes a communication system node 110A. In this regard, the first node arrangement of FIG. 3A is operable to provide backseat sensing with the dual-mode system nodes 110B at the second location and the third location. Meanwhile, the second node arrangement of FIG. 3B is operable to provide driver seat sensing with the dual-mode system node 110B at the fourth location and backseat sensing with the dual-mode system nodes 110B at the second location and the third location. In this regard, FIG. 3A and FIG. 3B show examples of how the dual-mode system nodes 110B and the communication system nodes 110A may be strategically used together to generate sensor fusion data, thereby enabling various sensing state data to be generated to benefit various in-vehicle sensing applications.

A UWB signal transmitted and received by nodes 110 can contain a packet or message, such as those described in U.S. Pat. Nos. 10,573,104 and 11,402,485 which are incorporated by reference herein in its entirety. In particular, the processors described herein are configured to processes CIR metadata to determine, for example, vital signs such as breathing rates and patterns of occupants in the vehicle. The processing system may operate on a given radio frequency (RF) signal property (e.g., channel information during communication) like CIR metadata to determine a given operating state. In an embodiment, the CIR metadata provides diagnostic information that the processing system may use to determine whether a received RF signal received is operating under a line-of-sight (LOS) or non-line-of-sight (NLOS) operating state.

The system 100 may determine LOS and NLOS operating states by computing the difference between a first path of the CIR metadata and a peak path position of the CIR metadata. It is contemplated that the difference between the first path and peak path may be greater for NLOS conditions than for LOS operating states. The system 100 may also evaluate the confidence level of the CIR metadata to determine whether a LOS or NLOS operating states exists. It is also contemplated that system 100 may use CIR metadata to evaluate a likelihood of undetected early paths to determine whether a LOS or NLOS condition exists.

It is contemplated that system 100 may determine NLOS or LOS operating states using any one of the CIR metadata (i.e., first path and peak path index, probability of NLOS estimate, confidence level, or likelihood of undetected early paths) alone. It is also contemplated that system 100 may combine one or more of the CIR metadata to more accurately determine whether a LOS or NLOS operating states exists. Additional signal processing is disclosed herein that can be implemented and executed by the processor(s) described herein.

In-vehicle sensing enables new features for in-vehicle entertainment and advanced safety and security functions for cars. Understanding the health status of the driver and passengers can provide better and more intelligent in-vehicle assistance. Detecting the activity of living beings in the car can also prevent unattended children being left behind in the vehicle, which unfortunately happens all too often and can cause heatstroke and/or death. A fundamental goal of this disclosure is for vital sign detection and estimation, which can enable in-vehicle sensing applications such as the following: driver/passenger vital signs monitoring, driver/passenger health and emotional status estimation, driver/passenger stress level estimation and sudden disease detection, occupancy detection, child-left-behind detection, object classification based on vital sign estimation.

Figure 4:
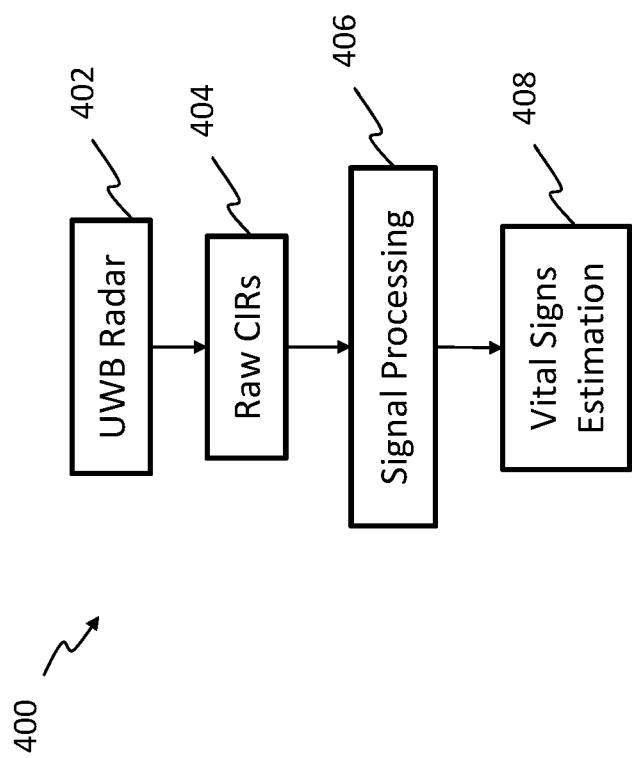
FIGS. 4-11 are illustrative operational diagrams of the vehicle system, according to various example embodiments of this disclosure.

The health detection concepts described herein can leverage the UWB signal processing described herein. The system disclosed herein has two main features. First, the ability to detect and classify different types of human activities by processing the UWB signals. Second, the ability to detect breathing, analyze breathing patterns, and estimate breathing rates. To perform such features, the system provided herein implements vital signs detection and estimation using UWB radar, the main system architecture of which is shown in FIG. 4. Here, the system 400, as with the other systems described herein, can be implemented by or with the system 100 described above with reference to FIG. 1. At 402, the system transmits and receives UWB radar, for example to and from the nodes 110. The UWB is a radio technology using low energy and high-bandwidth for short-range signal transmission and reception. In an embodiment, the UWB radar operates in 6 to 8.5 GHz frequency band with 500 MHz bandwidth. At 404, the radar transmitter of one node transmits impulse signals, and the radar receiver of another node receives the impulse responses as complex channel impulse responses (CIRs). At 406, the raw CIRs can be processed. Each CIR can be analyzed in defined time windows. At 408, based on the CIR signal processing, vital signs can be estimated. This can include breathing rate estimation and breathing pattern extraction.

Figure 5:
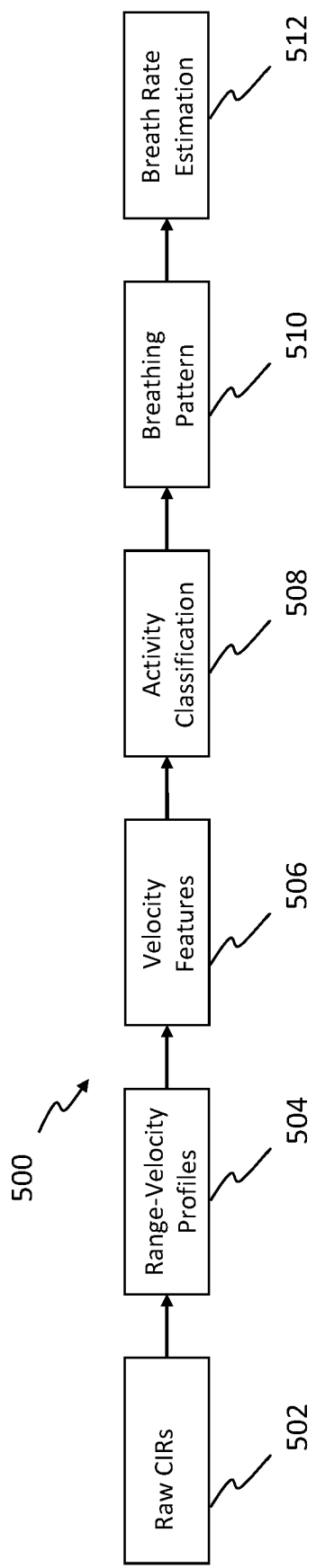

FIG. 5 depicts an operational flow diagram 500 for how the system 100 can be used for conducting a velocity-based breathing detection method. In this embodiment, the system 100 utilizes a method based on velocity features calculated using raw radar CIR data. Here, velocity features are used to determine the activity type of a subject in front of the radar nodes. Once a breathing activity is identified, the amplitude changes of the velocity features are leveraged over slow time to extract the breathing pattern. The breathing rate can be estimated using a Fast Fourier Transformation (FFT) calculation on breathing patterns over slow time.

At 502, the CIRs are generated periodically. The time between two consecutive CIRs is referred to herein as "slow time," whereas the sampling interval of each CIR is referred to herein as "fast time". Each sample in CIR is referred as a "tap". First, a 2D array can be constructed to include multiple CIRs in slow time where each CIR has multiple taps in fast time. The design of the 2D array enables the system to analyze a single CIR over multiple taps, as well as the changing of a certain tap over multiple CIRs.

In one embodiment, each raw radar CIR consists of 64 taps, and each tap of the CIR is 4 bytes. If the whole CIR is analyzed, that is 256 bytes. If the truncated CIR (e.g., 12-25 taps) are analyzed, that is 48-100 bytes.

At 504, range-velocity profiles are generated based on the raw radar CIRs. When a vehicle occupant's chest moves up and down from breathing, it moves with a certain velocity. So here, the system is observing the velocity of movement as indicated by the CIR. Range-velocity profiles are also referred as range-doppler profiles and FFT profiles, as they are generated by applying a discrete Fourier transform on each tap of CIRs over slow time. This process will result a doppler spectrum for each CIR tap over a pre-defined time window. From the range-velocity profiles, the system can obtain both ranges (CIR taps in fast time) and velocities (doppler spectrum in slow time) information. The system further truncates the range-velocity profiles in both fast time and doppler spectrum domains. For the truncation in fast time domain, the system selects the taps within a certain distance range to get reflected signals from intended targets. For the truncation in doppler spectrum domain, the system uses positive frequencies. Each range-velocity profile is generated from consecutive CIRs buffered on the receive/PC side. The result of range-velocity profile is stored on the memory of the receiving node, or the storage of the vehicle, or the storage of a remove computer and updated periodically.

In an embodiment, each range-velocity profile requires to buffer 32-128 CIRs. In a worst case, the number of FFTs for processing would be 64, therefore requiring a memory of 8.2-32.8 KB. With truncated CIRs, the number of FFTs for processing would be 12-25 FFTs, requiring a reduced memory of 1.6-12.8 KB.

In an embodiment, the system can use a calibration method to remove the static noise from the environment. During the calibration process, an average FFT profile from a static environment is generated. The average of the FFT amplitude and the total energy of the doppler spectrum for each tap of the CIR are generated from the calibration FFT profile. The system then uses this calibration FFT profile to do clutter reduction for incoming CIRs. The calibration FFT profile is subtracted from subsequent FFT profiles generated from later CIRs.

At 506, velocity features are determined based on each point of location along the velocity profile. The individual velocity features of each point can be extracted from the CIR or range-velocity profile and stored in storage. After calibration (if provided), and range-velocity profile generation, the system calculates a vector of velocity features from each range-velocity profile. These velocity features can include the following: velocity mean (e.g., the average of all velocities for each CIR tap in range-velocity profile), velocity mean after calibration (e.g., the average of all velocities for each CIR tap in range-velocity profile with the average of all velocities in calibration range-velocity profile subtracted), velocity energy (e.g., the total energy (square sum) of all velocities for each CIR tap in range-velocity profile), velocity energy after calibration (e.g., the total energy (square sum) of all velocities for each CIR tap in range-velocity profile with the total energy of all velocities in calibration range-velocity profile subtracted), and normalized velocity energy for calibration (e.g., the velocity energy after calibration with its mean over all CIR taps subtracted).

At 508, an activity classification model is executed. An objective of the activity classification model is to determine the status of a person. In an example in which breathing of a person is desired to be analyzed, since movement of the person can interfere with breathing detection, a goal of the system is to remove this other movement so that the system can focus on processing just the data associated with chest movement, for example. So first, the activity classification model can classify the person based on the person's overall movement.

The activity classification model is mainly based on analysis of the velocity features from 506. Within each range-velocity profile, the system selects the top n CIR taps with the maximum velocity energy after calibration. In an embodiment, the number n is equal to three by default. Then, the mean velocity energy is calculated for the top n CIR taps. This mean velocity energy can be referred to as activity level. The system further defines different threshold values for different activity classes based on different target environment. The activity classification is generated based on comparing the activity level with different threshold values.

In one embodiment, the different activity classes can include active, breathing, and static. For the active class, according to an embodiment, if the activity level is above an active threshold (e.g., lower threshold), the subject is classified as active. The active class means the subject is moving around (above a movement threshold), or the environment contains too much dynamic signals.

For the breathing (or breath) class, according to an embodiment, if both of the following conditions are met, the system can classify the subject as having a breathing activity: (1) activity level is below the active threshold but above a breathing threshold (e.g., upper threshold) and (2) the difference of the maximum energy among all CIR taps and the mean energy among all CIR taps is larger than a predefined threshold.

For the static class, according to an embodiment, all other conditions that do not satisfy either the active class or breathing class will be considered static.

The classification result can be generated for each range-velocity profile and stored as a numerical value along with the activity level. This numerical value for the activity classification result is referred to as an activity tag. The activity tag values for all range-velocity profiles in the range-velocity profile buffer can be stored in a buffer, such as a first in first out (FIFO) buffer. Meanwhile, a list of dominant taps to which the index of the tap with maximum energy among all CIR taps in a range-velocity profile is added if the activity tag is determined to be breath. In order to make a prediction of the activity type over longer period, the mean of activity tag values of individual range-velocity profiles is taken over various time intervals. For example, a sample decision flow chart is, in an embodiment: if the mean of the activity tag values over the last 10 seconds is within two predefined thresholds, the breath tag is set to true; If the mean of the activity tag values over the last five seconds is outside of another set of predefined thresholds, the breath tag is reset to false; If the mean of the activity tag values of the last three seconds is outside of yet another set of predefined thresholds, the breath tag is reset to false as well.

In an embodiment, the system can then proceed to select the dominant tap. The concept here is that each tap is one particular value, and each tap indicates one distance away from the sensor. If noise or other movement is far away, it can be removed because it is not within the dominant tap. For example, if the breath tag for the current range-velocity profile buffer is true and a minimum number of range-velocity profiles in the buffer have been classified with the breathing activity tag, then the CIR tap index that occurs most frequently in the list of dominant taps indices is selected. This tap along with two adjacent taps are finally considered to be the dominant tap, and used for further breathing pattern extraction and breathing rate estimation.

At 510, a breathing pattern associated with target occupant is extracted from the wireless signal. In general, the system looks to the velocity over time to get the average breathing pattern or rate. In an embodiment, the velocity energies for the three dominant taps from each range-velocity profiles in the buffer are extracted. The mean over these three taps is computed and recorded over slow time. This yields the person's breathing patterns. Also, the distance from the target to the UWB radar sensor is calculated using the dominant taps.

At 512, the system estimates the breathing rate of the target occupant. In an embodiment, the system applies a bandpass filter on the extracted breathing patterns to filter out the DC and high-frequency components. Thereafter, the filtered breathing patterns are transformed into the frequency domain using an FFT function. The frequencies at which the three frequency spectrum reach their respective maximum are found, with the average of these three frequencies representing an estimate of the subject's breathing rate.

The above approach enables the processing of UWB radar signals to determine a velocity of movement (e.g., chest movement) of a subject vehicle occupant in order to classify the activity of a subject vehicle occupant and estimate a breathing rate of that occupant. The use of UWB radar signals allows these computations to be done with less complexity and lower cost compared to other methods, such as the processing of frequency-modulated continuous wave (FMCW) radar. These teachings can also be utilized to determine the presence of a child in a backseat of the vehicle, the breathing rate of the baby, and the like.

Figure 6:
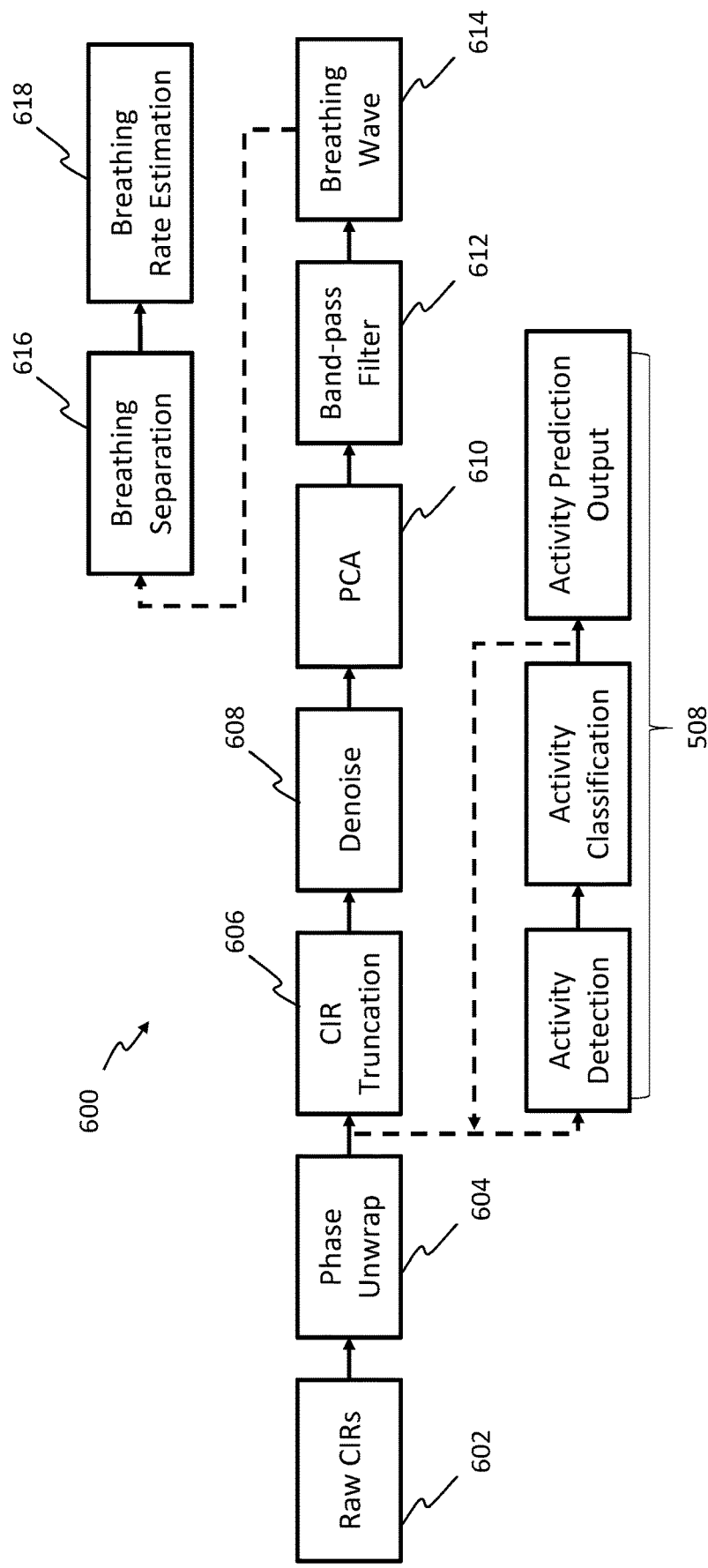

FIG. 6 depicts an operational flow diagram 600 for how the system 100 can be used for conducting a phase-based breathing detection method, according to an embodiment. Unlike the embodiment of FIG. 5, herein this embodiment, the system 100 utilizes a method based on the phase features of the raw CIR data of the UWB radar signals. Here, features of the signal's phase are used to determine the activity type of a subject in front of the radar nodes, the breathing rate of the subject, and the like as described above.

At 602, the system receives raw CIRs as input, similar to 502 in FIG. 5. A set of incoming CIRs are received that are arranged in fast and slow time is formatted as a 2D array. The system uses this 2D array as the input to the phase-based method.

At 604, the system performs a phase unwrap. In order to obtain continuous phase variation patterns, the system performs phase unwrapping by adding or subtracting appropriate multiples of 2π to remove the discontinuity of phase signal, according to an embodiment.

At 606, the system performs CIR truncation. Truncation of CIRs refers to the process of limiting or cutting off the length of the CIRs to a discrete sample size of number of CIR taps. To remove the noise from faraway reflections, the system truncates the CIR in fast-time domain. In an embodiment, the truncation is done by selecting a chunk of CIR taps which can cover all multipath components of the target environment. Also here, the breathing activity detection, subsequent activity classification, and activity prediction output described above with reference to FIG. 5 (e.g., step 508) can be performed likewise here in FIG. 6.

At 608, the system performs a denoise in which the system removes the static components in the target environment.

At 610, the system performs Principle Component Analysis (PCA). The target person's breathing pattern can be obtained from multiple CIR taps due to multipath effect in the target environment. To build a robust system, the phase analysis performed is not based on single tap of the CIR at the correct distance from target. Instead, the system uses all CIR taps after truncation and performs a PCA transformation to get a clean signal.

In embodiments, the PCA transformation is described as follows. First, the system identifies the hyperplane that lies closest to the data points. Then, the system selects the axis that accounts for the largest amount of variance as the principal components. In an embodiment, the system uses a standard matrix factorization technique called Singular Value Decomposition (SVD) to get the principal components:

$$X = U\Sigma V^T$$

where V contains the unit vectors that define all principal components. Then, the data is projected onto the target hyperplane.

At 612, the system applies a band-pass filter to remove DC and high frequency components in slow time.

The result is a breathing wave at 614. This can be visualized as a stream of data points that rise and fall as the target's chest moves up and down due to breathing. Data points associated with this movement yield movement of the body. At 616, the system can separate the data points into breaths. In an embodiment, the inflection point of the data points represent the moment in which the person stops inhaling and starts exhaling, or stops exhaling and starts inhaling. These can be the peaks and valleys of the breathing wave. This also allows the system to perform a breathing rate estimation at 618, which is based on the distance between the peaks or valleys over time. The breathing rate estimation 618 can be similar to 512 of FIG. 5.

Figure 7:
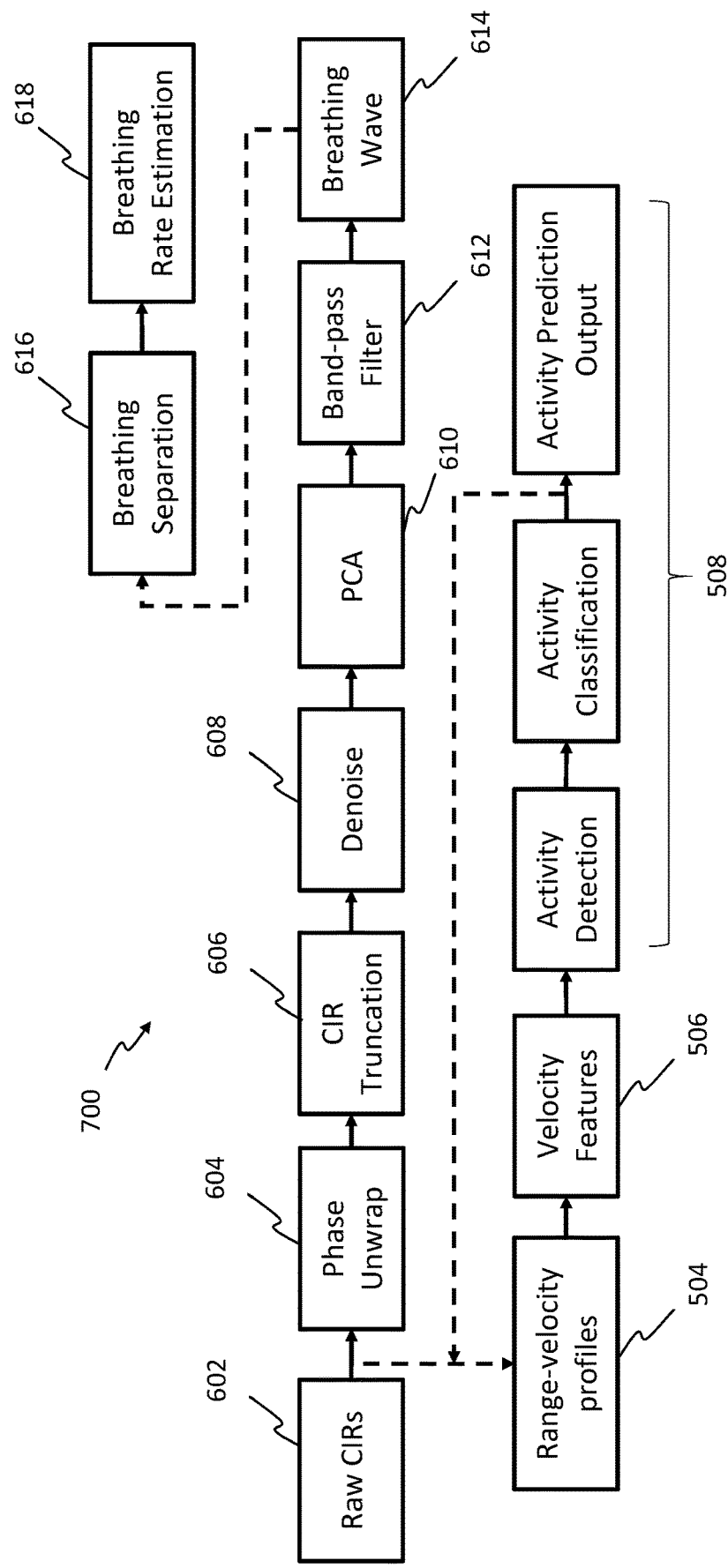

FIG. 7 depicts an operational flow diagram 700 for how the system 100 can be used for conducting a hybrid of the velocity-based breathing detection methods and the phase-based breathing detection methods, according to an embodiment. Here, the range-velocity profiles 504 and velocity features 506 are used for activity detection, classification and prediction output 508 as described in FIG. 5, and are brought into the system prior to performing a phase unwrapping at 604, for example. In this embodiment, the system utilizes the velocity-based method for detecting activities and determining the presence of a life form, and then the system continues with the phase-based approach to determine breathing patterns and estimate breathing rates of that detected life form.

Figure 8:
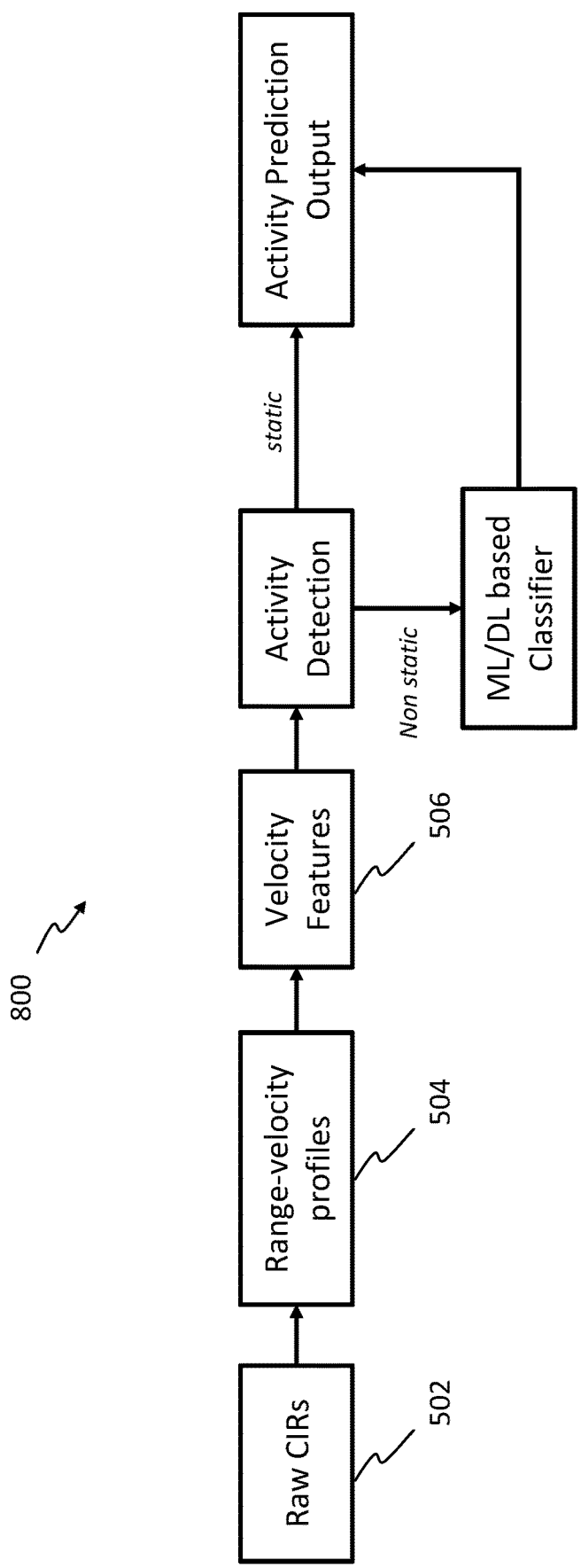
Figure 9:
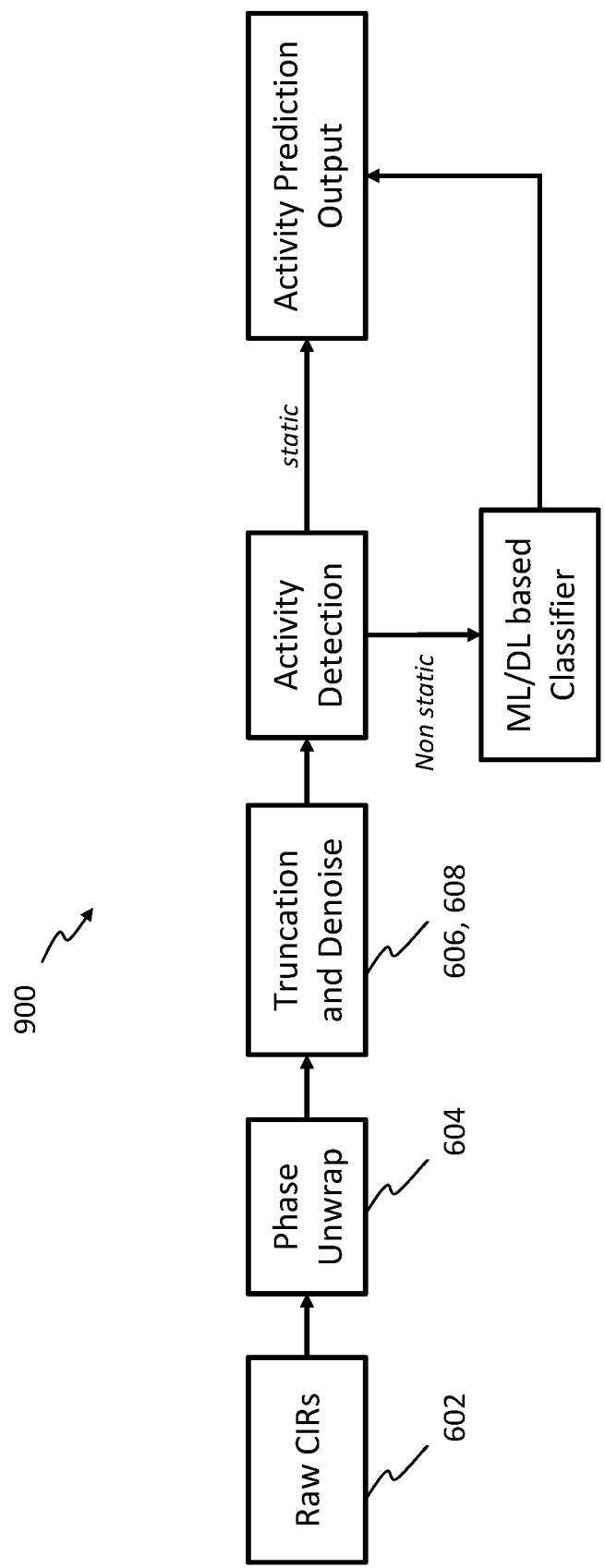
Figure 10:
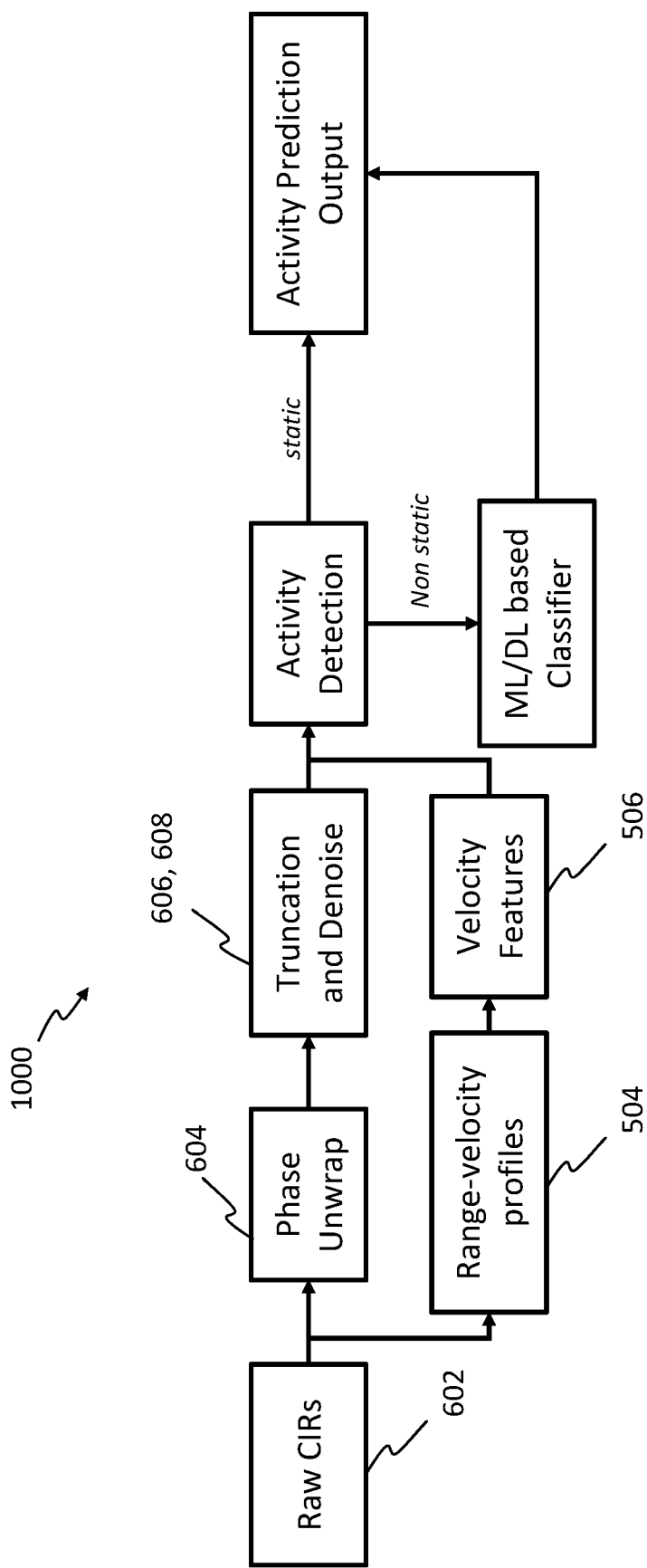

It should be understood that the methods and systems described herein can rely on machine learning (e.g., classification and deep learning). For example, FIG. 8 represents an operational flow diagram 800 for how the system 100 can be used for conducting a machine learning-based activity classification in which machine learning (ML) and/or deep learning (DL) models are utilized for activity classification, according to an embodiment. The machine learning can be executed on the non-static data (e.g., active and breath) as described above, and the ultimate predicted activity can rely on this ML/DL output along with the static data from the activity detection. It is contemplated that the machine-learning algorithm may employ known machine-learning classification algorithms like linear classifiers, support vector machines, decision trees, boosted trees, random forest, neural networks, or nearest neighbor. In FIG. 8, the ML-based activity classification uses velocity information (e.g., signal processing) while the ML (e.g., DL) is used for activity classification. FIG. 9 illustrates another embodiment in which ML is used on the phase-based data, wherein the activity detection uses phase information (e.g., signal processing) while the ML (e.g., DL) is used for activity classification. FIG. 10 illustrates another embodiment in which an ML-based architecture is used with both velocity and phase information; activity detection is performed using both velocity and phase information (e.g., signal processing) while ML is used for activity classification.

Figure 11:
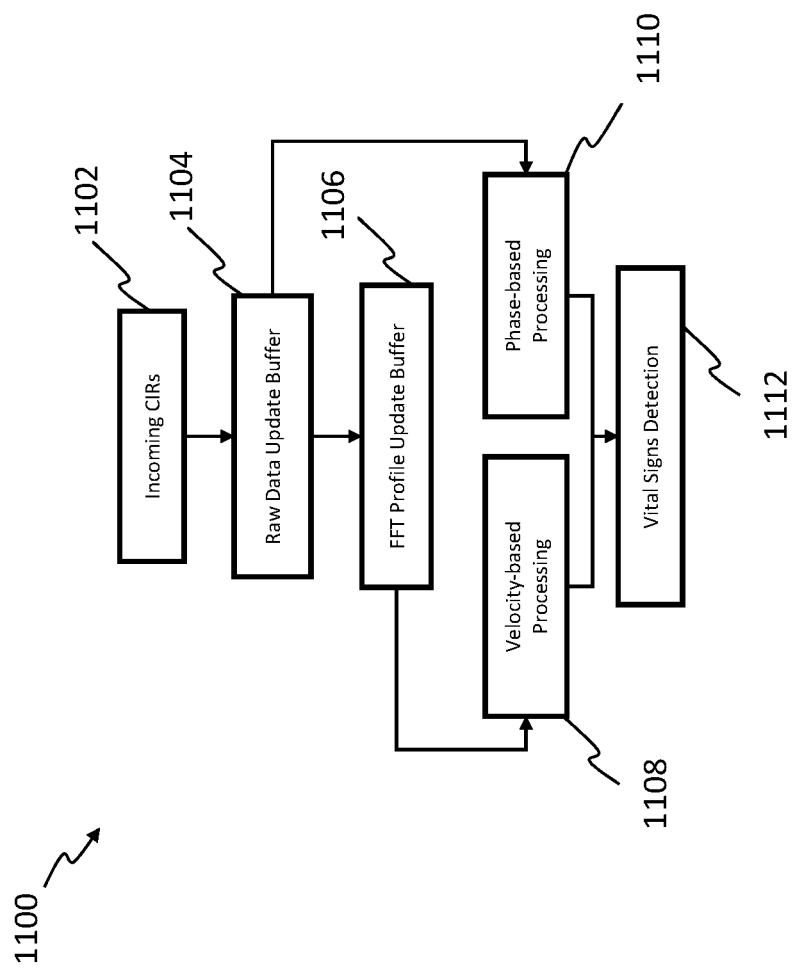

FIG. 11 illustrates a summary of the system architecture of system 100 for real-time implementation of the system, according to an embodiment. Data acquisition and signal processing can be implemented as daemon module running on a PC or embedded system, for example. The main application process creates multiple sub-daemon threads for data buffering and signal processing. At 1102, incoming CIRs are received from UWB radar devices. At 1104, a raw data update buffer thread stores the CIRs in a (e.g., fixed length) FIFO buffer. The new incoming data can overwrite the old data. At 1106, the FFT profile update buffer thread takes multiple CIRs from the raw data update buffer, performs FFT calculations for each tap of the CIR over slow time, and stores the FFT profile in a (e.g., fixed length) FIFO buffer. At 1108, a velocity-based processing module performs the velocity-based signal processing described herein, and at 1110 a phase-based processing module performs the phase-based signal processing described herein. At 1112, vital signs detection is performed on the raw data update buffer and the FFT profile update buffer and stores the vital signs results in a FIFO buffer.

The various steps and logic performed herein can be executed with non-volatile storage, memory, and processors. Non-volatile storage may include one or more persistent data storage devices such as a hard drive, optical drive, tape drive, non-volatile solid-state device, cloud storage or any other device capable of persistently storing information. Processor may include one or more devices selected from high-performance computing (HPC) systems including high-performance cores, microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on computer-executable instructions residing in memory. Memory may include a single memory device or a number of memory devices including, but not limited to, random access memory (RAM), volatile memory, non-volatile memory, static random access memory (SRAM), dynamic random access memory (DRAM), flash memory, cache memory, or any other device capable of storing information.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A method of estimating vital signs of vehicle occupants using Ultra-Wideband communication, the method comprising:
    transmitting Ultra-Wideband (UWB) signals from a first UWB system node within a vehicle;
    receiving the UWB signals at a second UWB system node within the vehicle;
    computing channel impulse responses (CIRs) associated with the UWB signals received at the second UWB system node;
    based on the CIRs, calculating velocities associated with the UWB signals;
    classifying an activity of a vehicle occupant as breathing based on the calculated velocities falling between a lower threshold and an upper threshold; and
    estimating a breathing rate of the vehicle occupant based on the calculated velocities.

2. The method of claim 1, further comprising:
    generating range-velocity profiles associated with the CIRs, wherein the velocity features are calculated based on the range-velocity profiles.

3. The method of claim 2, further comprising:
    calculating a vector of velocity features associated with the UWB signals, wherein the vector of velocities include (1) the calculated velocities associated the UWB signals and (2) an average of velocities for each CIR tap in the range-velocity profiles.

4. The method of claim 1, wherein the lower threshold is a breath threshold and the upper threshold is an active threshold.

5. The method of claim 1, wherein the CIRs include a plurality of CIR taps, the method further comprising:
    selecting a dominant tap of the CIR taps, wherein the dominant tap represents one of the CIR taps that has higher velocity energies than the remaining CTR taps;
    wherein the breathing rate is estimated based on the velocity energies associated with the dominant tap.

6. The method of claim 5, further comprising:
    extracting a breathing pattern from the velocities energies associated with the dominant tap.

7. The method of claim 1, further comprising:
    triggering a warning to an operator of the vehicle breathing rate of the vehicle occupant.

8. The method of claim 1, wherein the first UWB system node and the second UWB system node are the same UWB system node.

9. The method of claim 1, further comprising:
    performing a phase unwrapping of phase features associated with the CIRs;
    truncating the CIRs to select a chunk of CIR taps;
    performing a principle component analysis (PCA) transformation on the chunk of CIR taps to project CIR data onto a hyperplane;
    applying a band-pass filter to the projected CIR data to remove high-frequency components associated with the projected CIR data, wherein the applying yields filtered projected CIR data; and
    estimating the breathing rate of the vehicle occupant based on the filtered projected CIR data.

10. A method of estimating vital signs of vehicle occupants using Ultra-Wideband communication, the method comprising:
    transmitting Ultra-Wideband (UWB) signals from a first UWB system node within a vehicle;
    receiving the UWB signals at a second UWB system node within the vehicle;
    computing channel impulse responses (CIRs) associated with the UWB signals received at the second UWB system node;
    performing a phase unwrapping of phase features associated with the CIRs;
    truncating the CIRs to select a chunk of CIR taps;
    performing a principle component analysis (PCA) transformation on the CIR taps to project CIR data onto a hyperplane;
    applying a band-pass filter to the projected CIR data to remove high-frequency components associated with the projected CIR data, wherein the applying yields filtered projected CIR data; and
    estimating a breathing rate of the vehicle occupant based on the filtered projected CIR data.

11. The method of claim 10, further comprising:
    subsequent to the truncating, denoising the chunk of CIR taps to remove static components associated with UWB signals reflecting within the vehicle.

12. The method of claim 10, wherein the performing of the PCA transformation includes:
    identifying the hyperplane as lying closest to the CIR data;
    selecting an axis that accounts for a largest amounts of variance in the CIR data; and
    projecting the CIR data associated with the axis onto the identified hyperplane.

13. The method of claim 12, wherein the selecting the axis includes using a Singular Value Decomposition (SVD) technique.

14. The method of claim 10, further comprising:
    based on the CIRs, calculating velocities associated with the UWB signals;
    classifying an activity of the vehicle occupant as breathing based on the calculated velocities falling between a lower threshold and an upper threshold; and
    estimating the breathing rate of the vehicle occupant based on the calculated velocities.

15. The method of claim 14, further comprising:
    generating range-velocity profiles associated with the CIRs, wherein the velocity features are calculated based on the range-velocity profiles.

16. The method of claim 15, further comprising:
    calculating a vector of velocity features associated with the UWB signals, wherein the vector of velocities include (1) the calculated velocities associated the UWB signals and (2) an average of velocities for each CIR tap in the range-velocity profiles.

17. A system configured to estimate vital signs of vehicle occupants using Ultra-Wideband communication, the system comprising:

a transmitting node operable to transmit Ultra-Wideband (UWB) signals;

a receiving node operable to receive the UWB signals, wherein the UWB signals include channel impulse responses (CIRs); and a processor in communication with transmitting node and the receiving node, wherein the processor is programmed to:

receive the UWB signals at the receiving node;

extract the CIRs from the UWB signals received at the receiving node;

based on the CIRs, calculate velocities associated with the UWB signals; and estimate a breathing rate of a vehicle occupant based on the calculated velocities.

18. The system of claim 17, wherein the processor is further programmed to:

utilize a machine learning model to classify an activity of the vehicle occupant as breathing based on the calculated velocities.

19. The system of claim 17, wherein the processor is further programmed to:

perform a phase unwrapping of phase features associated with the CIRs;

truncate the CIRs to select a chunk of CIR taps;

perform a principle component analysis (PCA) transformation on the chunk of CIR taps to project CIR data onto a hyperplane;

apply a band-pass filter to the projected CIR data to remove high-frequency components associated with the projected CIR data, yielding filtered projected CIR data; and estimate the breathing rate of the vehicle occupant based on the filtered projected CIR data.

20. The system of 19, wherein the performing of the PCA transformation includes:

identifying the hyperplane as lying closest to the CIR data;

selecting an axis that accounts for a largest amounts of variance in the CIR data; and projecting the CIR data associated with the axis onto the identified hyperplane.

* * * * *